US009282909B2

United States Patent
Wang et al.

(10) Patent No.: US 9,282,909 B2
(45) Date of Patent: Mar. 15, 2016

(54) MEASUREMENT DEVICE WITH ELECTROENCEPHALOGRAPHY AND ELECTROCARDIOGRAPHY FUNCTIONALITIES

(71) Applicant: Wistron Corporation, New Taipei (TW)

(72) Inventors: Chia-Yuan Wang, New Taipei (TW); Chi-Chan Chiang, New Taipei (TW); Ting-Wen Liu, New Taipei (TW); Chun-Chih Lai, New Taipei (TW); Chia-Liang Lai, New Taipei (TW)

(73) Assignee: Wistron Corporation, Hsichih, New Taipei (TW)

( * ) Notice: Subject to any disclaimer, the term of this patent is extended or adjusted under 35 U.S.C. 154(b) by 171 days.

(21) Appl. No.: 14/185,939

(22) Filed: Feb. 21, 2014

(65) Prior Publication Data

US 2015/0080696 A1 Mar. 19, 2015

(30) Foreign Application Priority Data

Sep. 13, 2013 (TW) .............................. 102133247 A

(51) Int. Cl.
*A61B 5/0408* (2006.01)
*A61B 5/0478* (2006.01)

(52) U.S. Cl.
CPC ........... *A61B 5/04085* (2013.01); *A61B 5/0478* (2013.01); *A61B 2560/0443* (2013.01)

(58) Field of Classification Search
CPC ............. A61B 5/0404; A61B 5/04085; A61B 5/0478; A61B 5/6814; A61B 5/6825; A61B 5/6826; A61B 2560/0425; A61B 2560/0468
USPC ................................................ 600/383, 393
See application file for complete search history.

(56) References Cited

U.S. PATENT DOCUMENTS

| 8,965,492 | B2 * | 2/2015 | Baker | .................. | A61B 5/0006 600/372 |
| 2003/0088167 | A1 * | 5/2003 | Fendrock | ............. | A61B 5/0408 600/372 |
| 2009/0124869 | A1 | 5/2009 | Hu | | |

* cited by examiner

*Primary Examiner* — Lee S Cohen
(74) *Attorney, Agent, or Firm* — Winston Hsu; Scott Margo

(57) ABSTRACT

A measurement device with electroencephalography (EEG) and electrocardiography (ECG) functionalities includes a first shell having ECG functionality and a second shell. The first shell includes a first contact and a second contact located at a first side of the first shell; and a third contact located at a second side of the first shell, wherein the second side of the first shell is substantially opposite to the first side of the first shell. The second shell includes a fixing device, for connecting with and fixing on the first shell; and a fourth contact, a fifth contact and a sixth contact, located at a first side of the second shell, for electrically connecting with the first contact, the second contact and the third contact respectively when the first shell is connected to and fixed on the fixing device, in order to perform EEG measurement.

15 Claims, 6 Drawing Sheets

MEASUREMENT DEVICE WITH ELECTROENCEPHALOGRAPHY AND ELECTROCARDIOGRAPHY FUNCTIONALITIES

BACKGROUND OF THE INVENTION

1. Field of the Invention

The present invention relates to a measurement device, and more particularly, to a measurement device capable of electroencephalography and electrocardiography functionalities.

2. Description of the Prior Art

The electroencephalography (EEG) is utilized for measuring brainwave signals. The EEG can amplify weak physiological signals generated in the human brain, and perform analysis and comparison on these signals; hence, the EEG is typically used for brain disease diagnosis or sleep quality monitoring. The electrocardiography (ECG) is a detection system for recording cardiac signals. The ECG can capture and record cardiac signals via electronic signals on the skin. In each heartbeat, polarization of cardiac cells may generate slight voltage variations at the surface of the skin; the ECG can record such variations, in order to assist with diagnosis of heart disease.

Modern EEG and ECG are measurement products with mono-functionality, i.e. there is no bio-electronic product which can integrate both EEG and ECG functionalities. If the EEG and ECG functionalities could be effectively integrated in a single device, the facility and usage of these products could be significantly enhanced.

Thus, there is a need to provide a measurement device integrating EEG and ECG functionalities. Related production costs could be reduced by modifying internal operation circuits and external designs of signal contacts, to effectively minimize the size of the products as well as create additional features. The range of application of this product would therefore be increased, which could help in reducing related healthcare costs.

SUMMARY OF THE INVENTION

It is therefore an objective of the present invention to provide a measurement device having both electroencephalography (EEG) and electrocardiography (ECG) functionalities, which is capable of receiving EEG signals and monitoring sleep quality in an EEG mode and receiving ECG signals in an ECG mode. Such a measurement device may also transmit the received signals to medical centers for subsequent analysis and processing.

The present invention discloses a measurement device with both EEG and ECG functionalities. The measurement device comprises a first shell having ECG functionality and a second shell. The first shell comprises a first contact and a second contact located at a first side of the first shell; and a third contact located at a second side of the first shell, wherein the second side of the first shell is substantially opposite to the first side of the first shell. The second shell comprises a fixing device, for connecting with and fixing on the first shell; and a fourth contact, a fifth contact and a sixth contact, located at a first side of the second shell, for electrically connecting with the first contact, the second contact and the third contact, respectively, when the first shell is connected to and fixed on the fixing device, in order to perform EEG measurement.

These and other objectives of the present invention will no doubt become obvious to those of ordinary skill in the art after reading the following detailed description of the preferred embodiment that is illustrated in the various figures and drawings.

DETAILED DESCRIPTION

Figure 1:
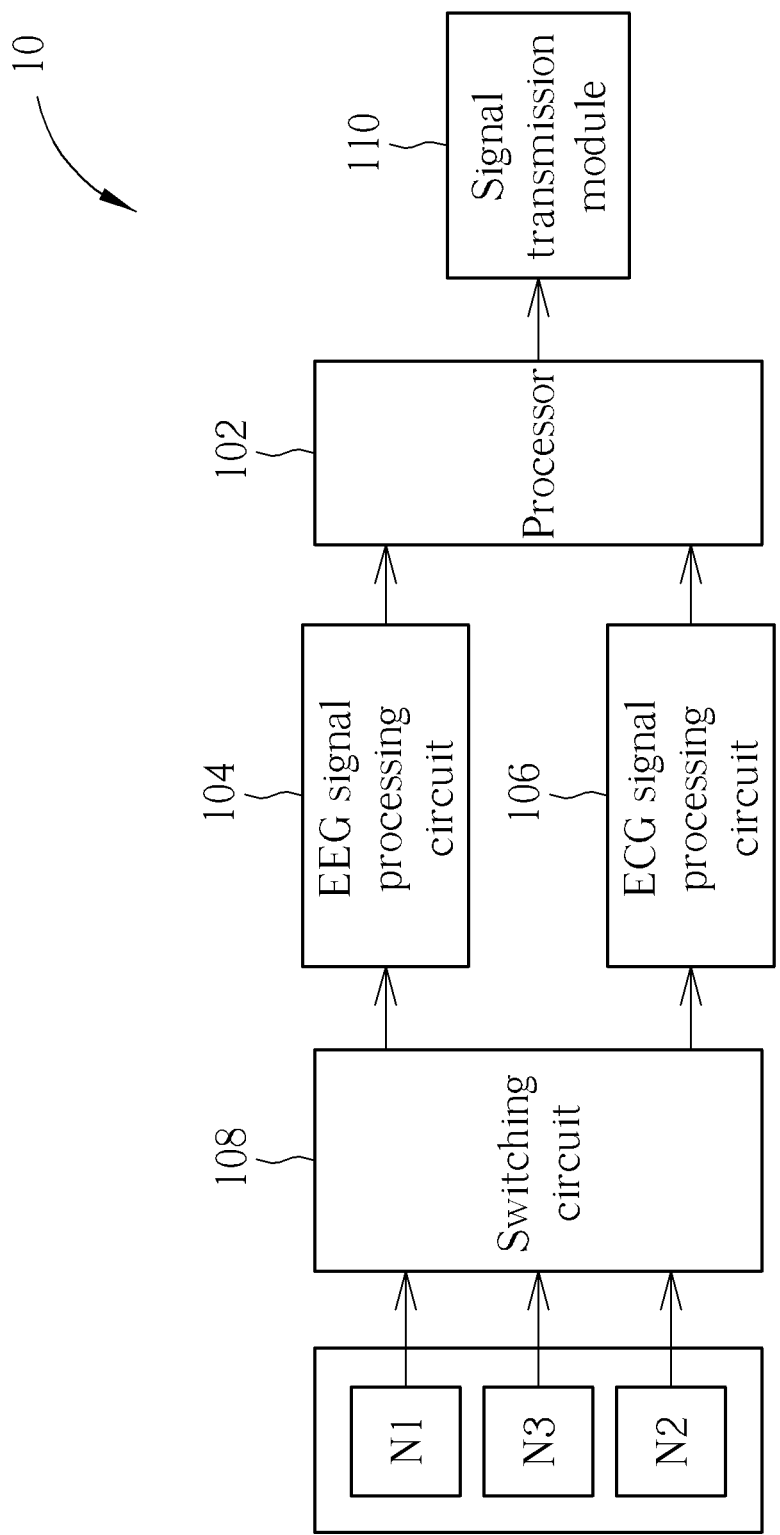
FIG. 1 is a schematic diagram of a circuit structure of a measurement device according to an embodiment of the present invention.

Please refer to FIG. 1, which is a schematic diagram of a circuit structure of a measurement device 10 according to an embodiment of the present invention. As shown in FIG. 1, the measurement device includes contacts N1-N3, a processor 102, an electroencephalography (EEG) signal processing circuit 104, an electrocardiography (ECG) signal processing circuit 106, a switching circuit 108 and a signal transmission module 110. The contacts N1-N3, located on the shell of the measurement device 10, are utilized for measuring physiological signals of a human body. When the measurement device 10 is in an EEG mode, the contacts N1-N3 may be placed on a user's forehead for receiving signals in order to perform EEG measurement and sleep management. When the measurement device 10 is in an ECG mode, the user may hold the measurement device 10 in their hand, e.g. by placing the right index finger, the left index finger and the left thumb on the contacts N1-N3, respectively, in order to perform ECG measurement. The sensing electrodes, composed of metal, conductive foam or other electrically conductive materials, may be disposed on the contacts N1-N3. For example, when the measurement device 10 is utilized for EEG measurement, the measurement device 10 is worn on the forehead of the user; hence the conductive foam may be utilized as sensing electrodes which touch the user's forehead, in order to increase the comfort of the user. When the measurement device 10 is utilized for ECG measurement, ergonomic materials such as metal may be applied.

The processor 102 is utilized for performing signal processing. The EEG signal processing circuit 104, coupled to the processor 102, is utilized for amplifying and filtering the signals received in the EEG mode. The ECG signal processing circuit 106, coupled to the processor 102, is utilized for amplifying and filtering the signals received in the ECG mode. The switching circuit 108 is utilized for switching the signal path. When the measurement device 10 is in the EEG mode, the switching circuit 108 controls the contacts N1-N3 to be coupled to the EEG signal processing circuit 104. When the measurement device 10 is in the ECG mode, the switching circuit 108 controls the contacts N1-N3 to be coupled to the ECG signal processing circuit 106. The signal transmission module 110, coupled to the processor 102, is utilized for transmitting signals to an external electronic device after the signals are interpreted by the processor 102. These signals will then be transmitted to a medical center via the Internet for subsequent analysis and processing. The signal transmission module 110 may use various wireless communication technologies such as Bluetooth or Wireless Fidelity (Wi-Fi) to transmit signals. The external electronic device may be any device with signal transmission functionality such as a laptop, tablet or smart phone.

In detail, the EEG and ECG having a single measurement channel may have three signal contacts, two of which may correspond to a pair of differential signals of the single measurement channel, the other corresponding to a reference signal. There is a signal processing circuit which can operate in an EEG or an ECG mode for processing EEG signals or ECG signals, respectively. In general, the signal processing circuit is utilized for filtering and amplifying signals. Since the strength and frequency of the EEG signals and the ECG signals are different, different signal processing circuits are required for each processing procedure. The measurement device 10 therefore comprises both the EEG signal processing circuit 104 and the ECG signal processing circuit 106 for processing EEG signals and ECG signals, respectively. The switching circuit 108 is further utilized for performing switching according to whether the measurement device 10 is in the EEG mode or the ECG mode.

Figure 2A:
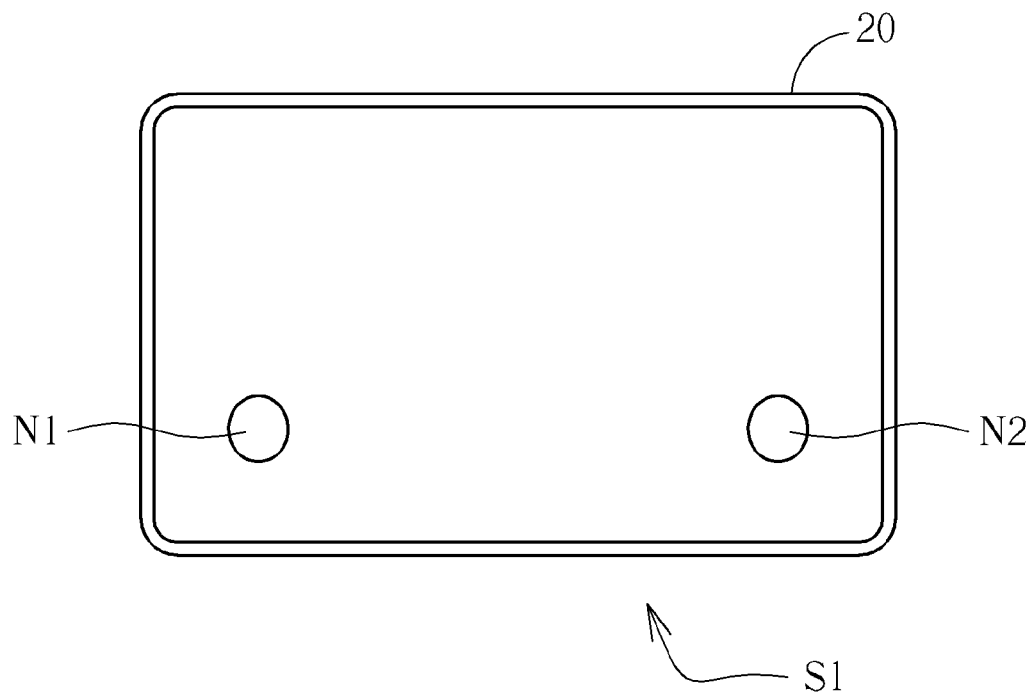
FIG. 2A and FIG. 2B are schematic diagrams of contacts disposed on a shell according to an embodiment of the present invention.
Figure 2B:
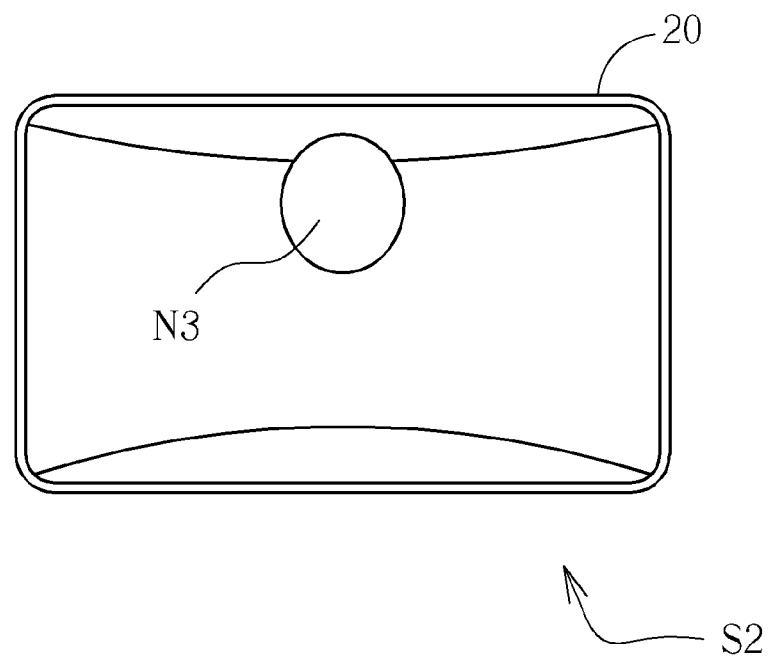

The disposition of the contacts N1-N3 may also need to be switched according to the measurement mode of the measurement device 10. Please refer to FIG. 2A and FIG. 2B, which are schematic diagrams of contacts N1-N3 disposed on a shell 20 according to an embodiment of the present invention. FIG. 2A illustrates a first side S1 of the shell 20, and FIG. 2B illustrates a second side S2 of the shell 20, where the second side S2 is substantially opposite to the first side S1. The abovementioned modules and structures of the measurement device 10 may be configured inside the shell 20. In this embodiment, when the user needs to perform ECG measurement, the user may hold the shell 20 in their hand by placing the right index finger, the left index finger and the left thumb on the contacts N1-N3, respectively. Since the user's right index finger, left index finger and left thumb correspond to the contacts N1, N2 and N3 respectively, the contacts N1 and N2 have to be located at the same side of the shell 20 (i.e. the first side S1), as shown in FIG. 2A, and the contact N3 has to be located at the side opposite to the contacts N1 and N2 (i.e. the second side S2), as shown in FIG. 2B. The user may hold the shell 20 on their hand allowing the contacts N1, N2 and N3 to transmit ECG signals of the user to the internal measurement device 10 for ECG measurement.

When the user needs to perform EEG measurement, the measurement device is worn on the forehead of the user. The three contacts N1-N3 should touch the forehead simultaneously, and therefore have to be located at the same side of the shell. According to the abovementioned disposition of the contacts N1-N3, however, the shell 20 of the measurement device cannot be utilized for performing EEG measurement by itself, and an additional device is therefore required for enabling the shell 20 to be used in EEG measurement.

Figure 3A:
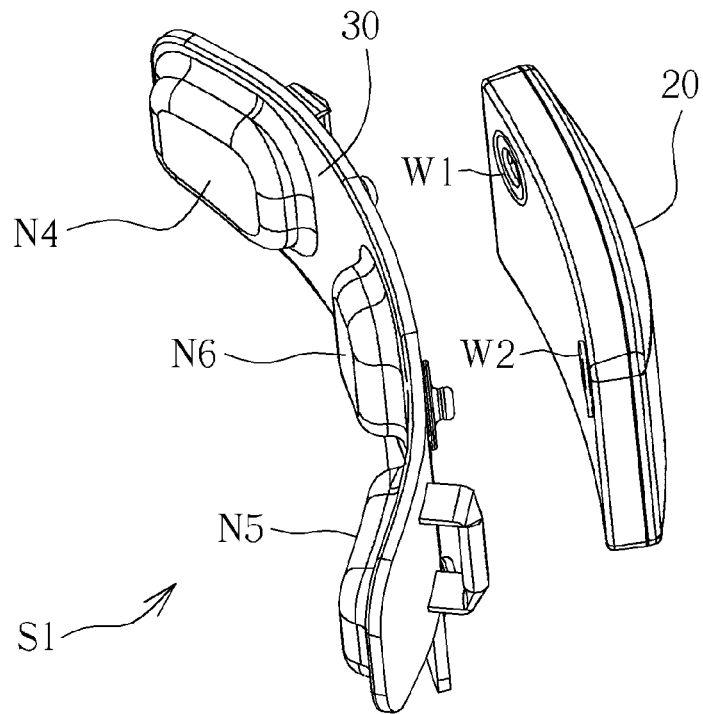
FIG. 3A and FIG. 3B are schematic diagrams of a shell connected to another shell.
Figure 3B:
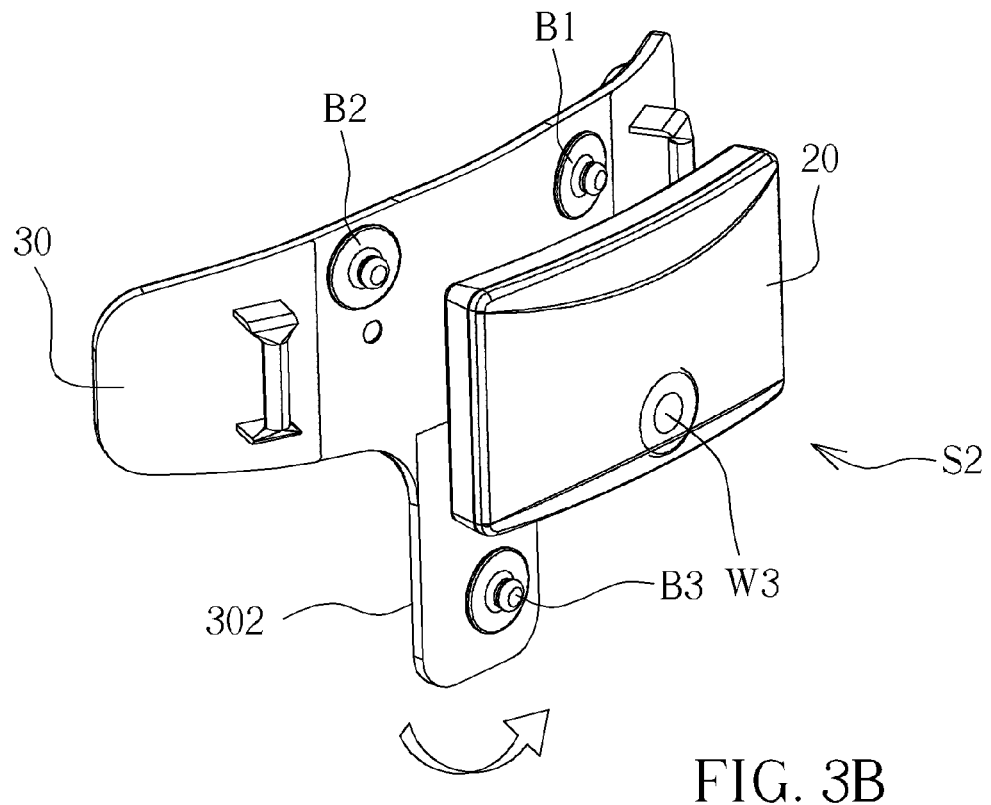

Please refer to FIG. 3A and FIG. 3B, which are schematic diagrams of the shell 20 connected to another shell 30. FIG. 3A and FIG. 3B respectively illustrate the shell connection front the first side S1 and the second side S2 of the shell 20. As shown in FIG. 3A and FIG. 3B, the shell 20 includes button fasteners W1, W2 and W3, respectively co-located with and electrically connected to the contacts N1, N2 and N3. The shell 30 includes buttons B1, B2 and B3, electrically connected to the contacts N4, N5 and N6, respectively. The contacts N4, N5 and N6 are located at the same side of the shell 30, which allows the user to easily perform EEG measurement, in this embodiment, when the user needs to perform EEG measurement, the user may connect and fix the buttons B1, B2 and B3 on the button fasteners W1, W2 and W3 respectively, so that the contacts N1, N2 and N3 can be coupled to the contacts N4, N5 and N6 respectively. As shown in FIG. 3A and FIG. 3B, when the buttons B1 and B2 are respectively buckled on the button fasteners W1 and W2, the button fastener W3 is located at the side opposite to the button fasteners W1, W2, so that button B3 cannot be directly buckled on the button fastener W3. A belt 302 can be disposed, wherein one terminal of the belt 302 may be connected to the shell 30 and the other terminal includes the button B3 When the buttons B1 and B2 are fixed on the button fasteners W1 and W2 located at the first side S1 of the shell 20, the user may further turn the belt 302 to the second side S2 of the shell 20, in order to fix the button 133 on the button fastener W3, so that the contacts N1, N2 and N3 can be coupled to the contacts N4, N5 and N6, respectively.

When the shell 20 is connected to and fixed on the shell 30, the contacts N4, N5 and N6 are located at the same side of the shell. The shell 30 can therefore be placed on the user's forehead and the contacts N4, N5 and N6 may touch the user's forehead simultaneously, in order to obtain EEG signals. In some embodiments, a head-mounted device may be utilized for fixing the shell 30 on the forehead. For example, the user may tie the shell 30 on their forehead via a headband. The head-mounted device may fix the shell 30 on the forehead by any methods, which are not limited herein.

Please note that, when the user performs EEG measurement, the contacts N4, N5 and N6 on the shell 30 are utilized for obtaining EEG signals and should be electrically connected to the contacts N1, N2 and N3 respectively, in order to transmit the signals to the measurement device 10 inside the shell 20. The buttons B1, B2 and B3 and the button fasteners W1, W2 and W3 should be realized by electrically conductive materials, so that the signals may be transmitted via the buttons B1, B2 and B3 and the button fasteners W1, W2 and W3 when the buttons B1, B2 and B3 are budded on the button fasteners W1, W2 and W3.

The above disposition of the contacts N1-N6 and the combination of the shells only represents one of various embodiments of the present invention. Those skilled in the art can make modifications and variations according to requirements. The purpose of disposing the contact N3 to be at the side opposite to the contacts N1 and N2 on the shell 20 and disposing the contacts N4, N5 and N6 to be at the same side of the shell 30 is to allow the user to conveniently measure the physiological signals in both the ECG mode and the EEG mode. In practice, the disposition of the contacts N1-N6 may not need to be at the same side or on exactly opposite sides. Instead, the position of the contacts N1-N6 may be adjusted ergonomically. For example, when the shell 20 is connected to and fixed on the shell 30 for EEG measurement, the contacts N4-N6 may not be disposed at the same flat surface, and may be adjusted according to the radian or the shape of the forehead. When the shell 20 is held in the user's hand for ECG measurement, the contact N3 may not be disposed in the middle place on the shell 20, and may be disposed on the left-hand side of the user, which allows the user to easily put their left thumb on the contact N3. The connection between the shell 20 and the shell 30 may be realized by any method or using any fixing device, and is not limited to the abovementioned method. For example, in the above embodiments, the buttons B1, B2 and B3 are disposed on the shell 30 and the button fasteners W1, W2 and W3 are disposed on the shell 20. In other embodiments, the disposition of the buttons and the button fasteners may be interchanged, as long as the shell 20 can be connected to and fixed on the shell 30 for EEG measurement.

Figure 4A:
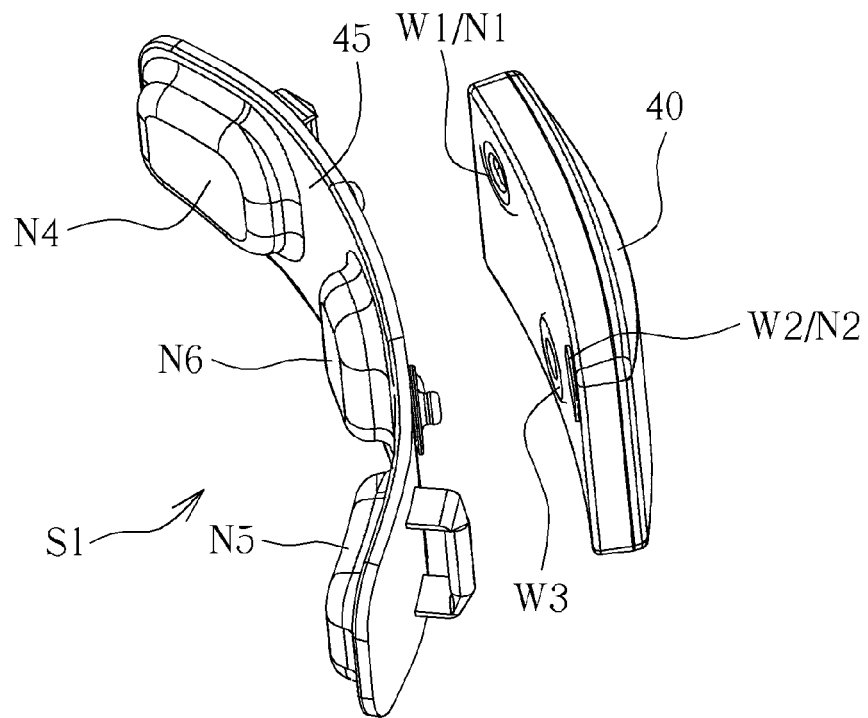
FIG. 4A and FIG. 4B are schematic diagrams of a shell connected to another shell according to an embodiment of the present invention.
Figure 4B:
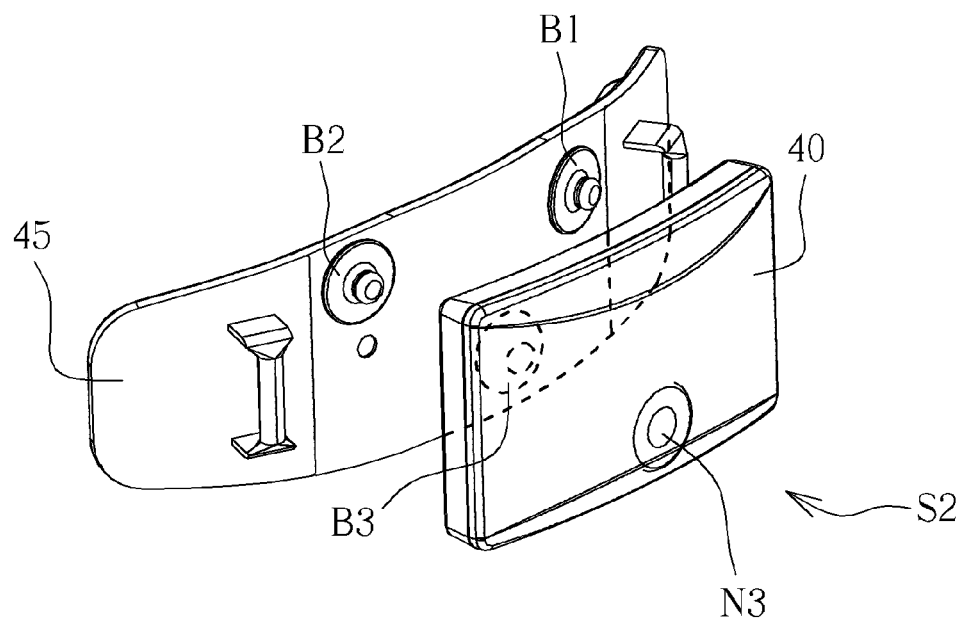

In an embodiment, the connection between the buttons B1, B2 and B3 and the button fasteners W1, W2 and W3 may not be realized via the belt 302. Please refer to FIG. 4A and FIG. 4B, which are schematic diagrams of a shell 40 connected to another shell 4 according to an embodiment of the present invention. FIG. 4A and FIG. 4B respectively illustrate the shell connection from a first side S1 and a second side S2 of the shell 40. As shown in FIG. 4A and FIG. 4B, the structure of the shell 40 is similar to that of the shell 20, where the shell 40 also includes contacts N1, N2 and N3 and corresponding button fasteners W1, W2 and W3. The main difference between the shell 40 and the shell 20 is that the button fasteners W1, W2 and W3 of the shell 20 are co-located with the contacts N1, N2 and N3 respectively, but in the shell 40, only two button fasteners W1 and W2 are co-located with the contacts N1 and N2 respectively and the button fastener W3 is located in a location different from the contact N3. On the shell 40, although the contact N3 is still located at the second side S2, the button fastener W3 is disposed at the first side S1. A signal transmission wire is utilized for connecting the button fastener W3 and the contact N3 inside the shell 40. Otherwise, the button fastener W3 should be electrically connected to the contact N3 by other methods to allow signals to be transmitted between the button fastener W3 and the contact N3. In other embodiments, both the button fastener W3 and the contact N3 may be respectively electrically connected to corresponding internal circuits allowing the operations in different measurement modes. For example, the contact N3 may be electrically connected to the ECG signal processing circuit 106, and the signal path corresponding to the contact N3 is enabled when ECG measurement is performed. The button fastener W3 may be electrically connected to the EEG signal processing circuit 104, and the signal path corresponding to the button fastener W3 is enabled when EEG measurement is performed.

The structure of the shell 45 is similar to that of the shell 30, where the shell 45 also includes contacts N4, N5 and N6 and corresponding buttons B1, B2 and B3. On the shell 45, the contacts N4, N5 and N6 are also located at the same side, so that the user may perform EEG measurement conveniently. Since the button fasteners W1, W2 and W3 are all located at the first side S1 of the shell 40, the buttons B1, B2 and B3 may be disposed at the same side of the shell 45 with locations corresponding to the button fasteners W1, W2 and W3, in order to be respectively buckled and fixed on the button fasteners W1, W2 and W3. Preferably, the buttons B1. B2 and B3 may be disposed opposite to the contacts N4, N5 and N6, so that the shell 40 may be worn on the user's forehead for EEG measurement when connected to and fixed on the shell 45.

In the above embodiments, the connection and fixing of two shells are realized by buttons and button fasteners. In other embodiments, other methods or other fixing devices may also be utilized for performing the fixing. The fixing device should be able to connect and fix on two shells. Preferably, the two shells may be installed and dismantled conveniently, so that the user can easily switch between different measurement modes. In some embodiments, the system may automatically detect whether two shells are connected with each other, in order to determine whether the measurement device is in the EEG mode or the ECG mode. The internal operation circuit may further be switched accordingly, in order to perform corresponding signal processing. For example, the measurement device 10 may include a detector element such as a tact switch or light sensing element which can automatically detect the connection status between two shells. The user therefore only needs to assemble or disassemble the two shells, and the system may be switched to a corresponding mode to perform measurement. In other embodiments, the measurement device 10 may include a manual switch for manually controlling the switching circuit 108 to switch between the EEG mode and the ECG mode. In further embodiments, the abovementioned external electronic devices may also be utilized for switching the measurement device 10 between the EEG mode and the ECG mode.

Figure 5A:
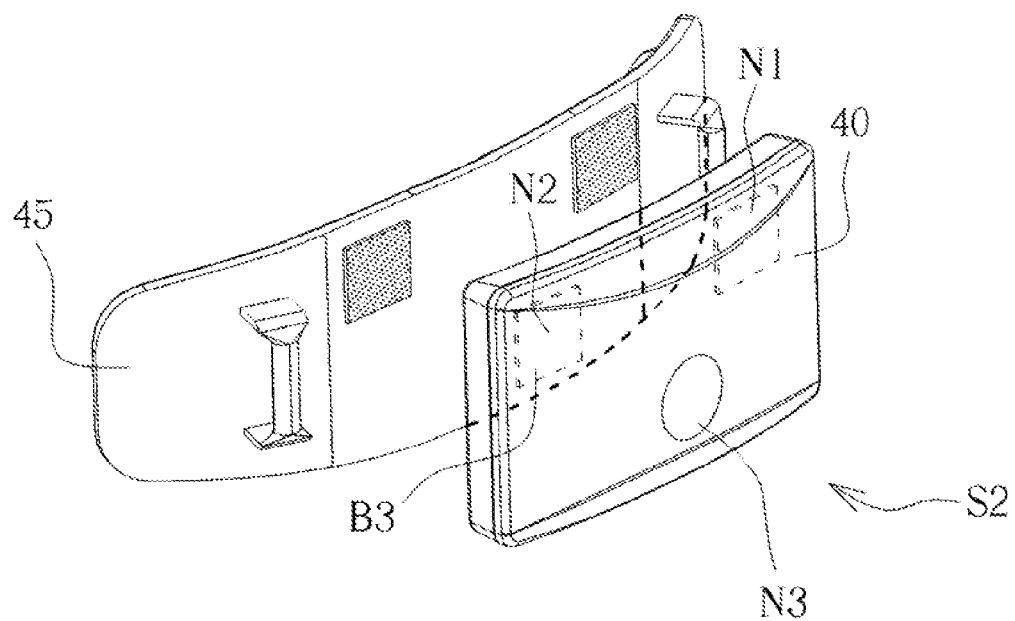
FIG. 5A, FIG. 5B and FIG. 5C are schematic diagrams of a shell connected to another shell according to embodiments of the present invention.
Figure 5B:
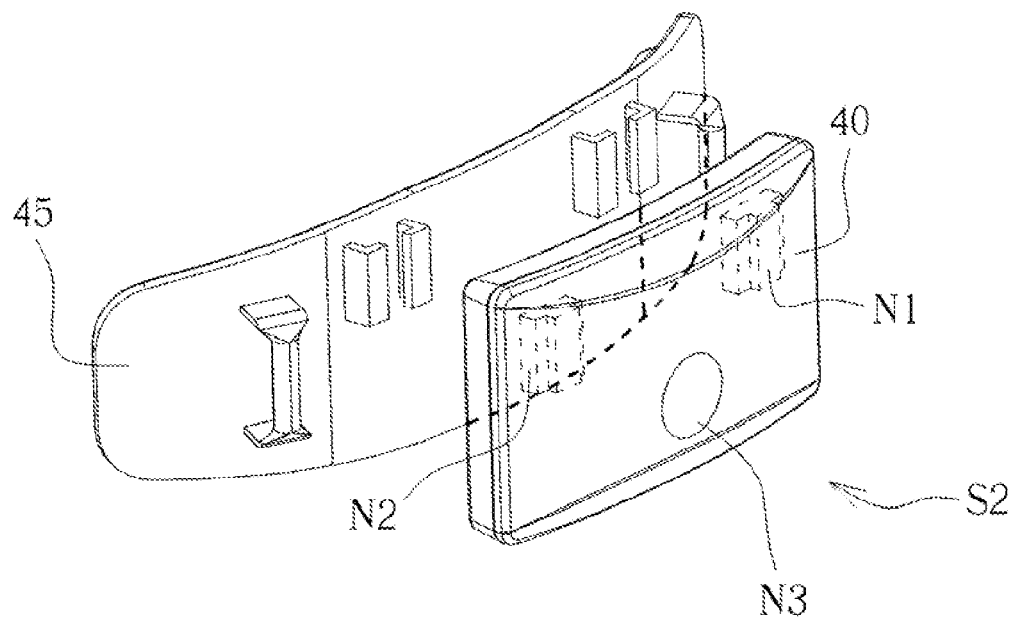
Figure 5C:
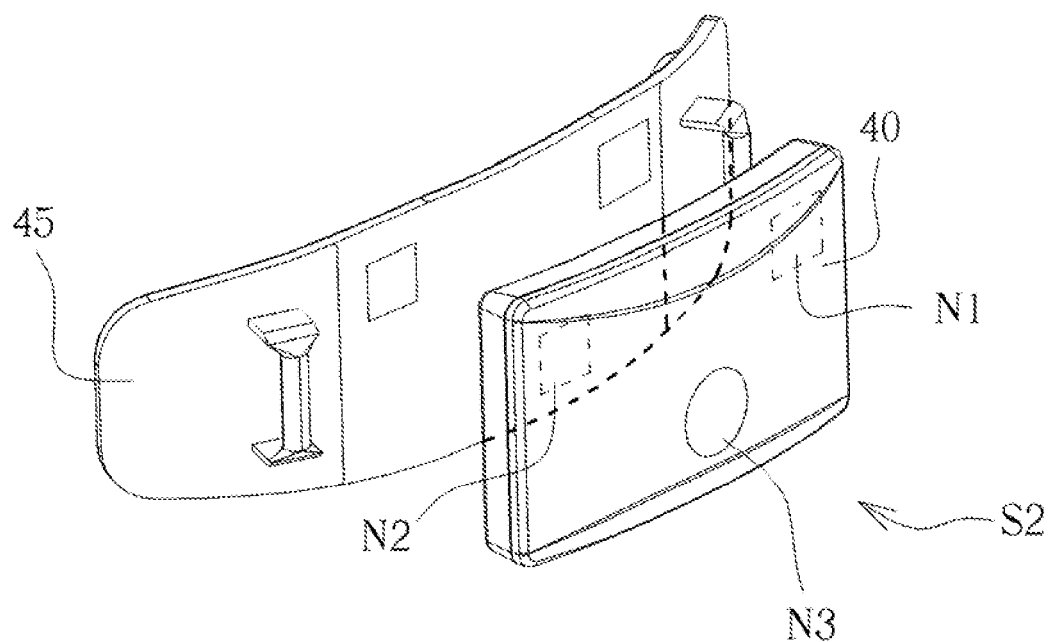

The abovementioned fixing device may be of any type, and can include a dovetail, magnet, Velcro strip or metal dome. For example, a dovetailed base may be installed on a shell, and the other shell may be inserted and fixed on the dovetailed base, where electrically conductive materials and a signal transmission path may be disposed at the connecting points between the two shells. In other embodiments, a magnet may be installed on a shell, in order to connect with and fix on the other shell via magnetic force. A Velcro strip may also be installed on a shell, in order to connect with and fix on the other shell via adherence. For example, FIG. 5A illustrates a shell 50 connected to another shell 51 via hook and loop fastener, i.e., Velcro strip, FIG. 5B illustrates a shell 52 connected to another shell 53 via dovetailed connector, and FIG. 5C illustrates a shell 54 connected to another shell 55 via magnetic force. As shown in FIGS. 5A-5C, the structures of the shells 50-55 are similar to those of the shells 40 and 45, so the components with similar functions are denoted by the same symbols. The main difference between these shells is in the connection media. The related implementations should be well-known by those skilled in the art, and will not be expanded upon herein.

In the prior art, the EEG and ECG are measurement products with mono-functionality, such that there is no bio-electronic product that can integrate both EEG and ECG functionalities. In contrast, the measurement device of the present invention can effectively integrate the functionalities of EEG and ECG by modifying internal operation circuits and external designs of signal contacts. This achieves the benefits of minimizing the size of the products, thereby increasing the willingness of a user to use the products, which could result in reducing healthcare costs.

Those skilled in the art will readily observe that numerous modifications and alterations of the device and method may be made while retaining the teachings of the invention. Accordingly, the above disclosure should be construed as limited only by the metes and bounds of the appended claims.

What is claimed is:

1. A measurement device with electroencephalography (EEG) and electrocardiography (ECG) functionalities, comprising:
    a first shell, having ECG functionality, comprising:
        a first contact and a second contact located at a first side of the first shell; and
        a third contact located at a second side of the first shell, wherein the second side of the first shell is substantially opposite to the first side of the first shell; and
    a second shell, comprising:
        a fixing device, for connecting with and fixing on the first shell; and
        a fourth contact, a fifth contact and a sixth contact, located at a first side of the second shell, for electrically connecting with the first contact, the second contact and the third contact respectively when the first shell is connected to and fixed on the fixing device, in order to perform EEG measurement.

2. The measurement device of claim 1, wherein the second shell comprises a head-mounted device, for being worn on a forehead of a user in order to perform EEG measurement.

3. The measurement device of claim 1, wherein the fixing device comprises at least one button, for connecting with and fixing on the first shell.

4. The measurement device of claim 1, wherein the fixing device comprises a first button, a second button and a third button, electrically connected to the fourth contact, the fifth contact and the sixth contact respectively, wherein the first button and the second button are located at a second side of the second shell wherein the second side of the second shell is substantially opposite to the first side of the second shell, and the third button is located in a first terminal of a belt wherein a second terminal of the belt is connected to the second shell.

5. The measurement device of claim 4, wherein the first shell comprises a first button fastener, a second button fastener and a third button fastener, respectively co-located with the first contact, the second contact and the third contact, and electrically connected to the first contact, the second contact and the third contact.

6. The measurement device of claim 5, wherein when the measurement device is utilized for performing EEG measurement, the first button and the second button are respectively connected to and fixed on the first button fastener and the second button fastener, and the first terminal of the belt is turned to the second side of the first shell in order to allow the third button to be connected to and fixed on the third button fastener.

7. The measurement device of claim 1, wherein the fixing device comprises a first button, a second button and a third button, electrically connected to the fourth contact, the fifth contact and the sixth contact respectively, wherein the first button, the second button and the third button are located at a second side of the second shell, and the second side of the second shell is substantially opposite to the first side of the second shell.

8. The measurement device of claim 7, wherein the first shell comprises a first button fastener, a second button fastener and a third button fastener, electrically connected to the first contact, the second contact and the third contact respectively, wherein the first button fastener, the second button fastener and the third button fastener are located at the first side of the first shell.

9. The measurement device of claim 8, wherein when the measurement device is utilized for performing EEG measurement, the first button, the second button and the third button are respectively connected to and fixed on the first button fastener, the second button fastener and the third button fastener.

10. The measurement device of claim 1, wherein the fixing device comprises a dovetailed base for fixing on the first shell.

11. The measurement device of claim 1, wherein the fixing device comprises a magnet, for connecting with and fixing on the first shell by magnetic force.

12. The measurement device of claim 1, wherein the fixing device comprises a hook and loop fastener, for connecting with and fixing on the first shell by adherence.

13. The measurement device of claim 1, wherein the first contact and the second contact correspond to a pair of differential signals of a measurement channel, and the third contact corresponds to a reference signal.

14. The measurement device of claim 1, further comprising an operation circuit disposed in the first shell, the operation circuit comprising:
a processor;
an EEG signal processing circuit, coupled to the processor;
an ECG signal processing circuit, coupled to the processor; and
a switching circuit, for controlling the first contact, the second contact and the third contact to be coupled to the EEG signal processing circuit when the measurement device performs EEG measurement, and controlling the first contact, the second contact and the third contact to be coupled to the ECG signal processing circuit when the measurement device performs ECG measurement.

15. The measurement device of claim 14, wherein the operation circuit further comprises a signal transmission module, coupled to the processor, for transmitting a signal to an external electronic device after the signal is interpreted by the processor.

* * * * *